(12) United States Patent
Wildsoet et al.

(10) Patent No.: US 8,883,214 B2
(45) Date of Patent: Nov. 11, 2014

(54) IMPLANTABLE DELIVERY VEHICLE FOR OCULAR DELIVERY OF MUSCARINIC ANTAGONISTS

(75) Inventors: Christine F. Wildsoet, Berkeley, CA (US); James Su, Berkeley, CA (US); Kevin E. Healy, Moraga, CA (US)

(73) Assignee: The Regents of the University of California, Oakland, CA (US)

( * ) Notice: Subject to any disclaimer, the term of this patent is extended or adjusted under 35 U.S.C. 154(b) by 82 days.

(21) Appl. No.: 13/144,065

(22) PCT Filed: Jan. 11, 2010

(86) PCT No.: PCT/US2010/020644
§ 371 (c)(1),
(2), (4) Date: Sep. 29, 2011

(87) PCT Pub. No.: WO2010/083129
PCT Pub. Date: Jul. 22, 2010

(65) Prior Publication Data
US 2012/0015035 A1  Jan. 19, 2012

Related U.S. Application Data

(60) Provisional application No. 61/144,372, filed on Jan. 13, 2009.

(51) Int. Cl.
*A61K 9/50* (2006.01)
*A61K 47/32* (2006.01)
*A61L 27/52* (2006.01)
*A61L 27/54* (2006.01)
*A61K 9/00* (2006.01)
*A61K 9/06* (2006.01)

(52) U.S. Cl.
CPC ......... *A61K 9/0051* (2013.01); *A61L 2300/432* (2013.01); *A61L 2430/16* (2013.01); *A61K 47/32* (2013.01); *A61L 2300/622* (2013.01); *A61L 27/52* (2013.01); *A61L 27/54* (2013.01); *A61K 9/06* (2013.01); *A61L 2300/624* (2013.01)
USPC ........................... 424/489; 514/220; 514/291

(58) Field of Classification Search
CPC ........ A61K 9/0051; A61K 9/06; A61K 47/32
USPC ..................... 424/489; 514/220, 291, 30, 322
See application file for complete search history.

(56) References Cited

U.S. PATENT DOCUMENTS

| | | | |
|---|---|---|---|
| 2005/0169882 A1* | 8/2005 | Lowe et al. | 424/78.27 |
| 2005/0271590 A1* | 12/2005 | Schwartz et al. | 424/9.5 |
| 2006/0188576 A1 | 8/2006 | Takruri et al. | |
| 2008/0241222 A1* | 10/2008 | Whitcup et al. | 424/428 |
| 2009/0104243 A1* | 4/2009 | Utkhede et al. | 424/423 |

OTHER PUBLICATIONS

Chou et al., Title: The effectiveness of 0.5% atropine in controlling high myopia in children; J. Ocul Pharmacol Ther. 13(1), pp. 61-67; published Feb. 1997, by PubMed.*
Product information of Pluronic F-127, published Jan. 9, 2008 by Invitrogen, Ltd.*
Su, et al. "Effects of poly(2-hydroeyethyl methacrylate) and poly (vinyl-pyrrolidone) hydrogel implants on myopic and normal chick sckera", *Exp Eye Res.* (2009), 88(3):445-457.

* cited by examiner

*Primary Examiner* — Johann R Richter
*Assistant Examiner* — Yanzhi Zhang
(74) *Attorney, Agent, or Firm* — Paula A. Borden; Bozicevic, Field & Francis LLP.

(57) ABSTRACT

The present invention provides compositions and methods for treating ocular disorders such as myopia.

20 Claims, 9 Drawing Sheets

IMPLANTABLE DELIVERY VEHICLE FOR OCULAR DELIVERY OF MUSCARINIC ANTAGONISTS

CROSS-REFERENCE

This application claims the benefit of U.S. Provisional Patent Application No. 61/144,372, filed Jan. 13, 2009, which application is incorporated herein by reference in its entirety.

STATEMENT REGARDING FEDERALLY SPONSORED RESEARCH

This invention was made with government support under Grant No. R01EY12392 awarded by the National Institutes of Health. The government has certain rights in the invention.

BACKGROUND

Degenerative myopia is a significant cause of world blindness and visual disability. Degenerative myopia is a major cause of legal blindness in the United States. Overall, blindness most commonly occurs from myopic macular degeneration, retinal detachment, cataract and glaucoma, and of these, myopic macular degeneration is the most important. Degenerative myopia is thought to be due to decompensation of the nerve and supporting tissues of the part of the retina of the eye, the macular, which is used for fine vision. One cause of the damage is the axial overgrowth of the eye during the regular growth phase, followed by further increments of stretching during the adult years. By middle age, stressed eye tissues begin to show degeneration and failure of function; crucially, this includes the delicate nerves of the retina.

Current treatments for high myopia progression include topical daily drops of muscarinic antagonists.

LITERATURE

U.S. Patent Publication No. 2006/0188576; Su et al. (2009) Exp. Eye Res. 88:445.

SUMMARY OF THE INVENTION

The present invention provides compositions and methods for treating ocular disorders such as myopia.

DEFINITIONS

Figure 1:
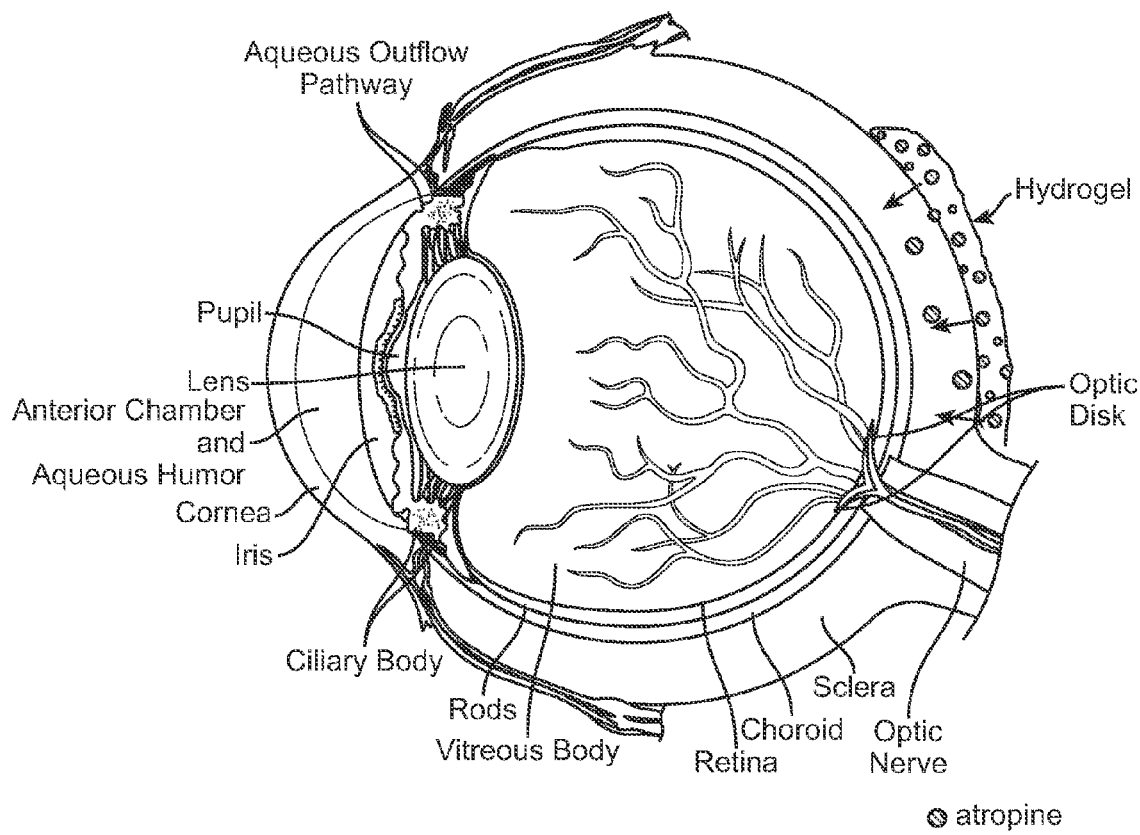
FIG. 1 depicts an exemplary embodiment of delivery of a muscarinic antagonist in a biodegradable hydrogel matrix through the posterior sclera.
Figure 2:
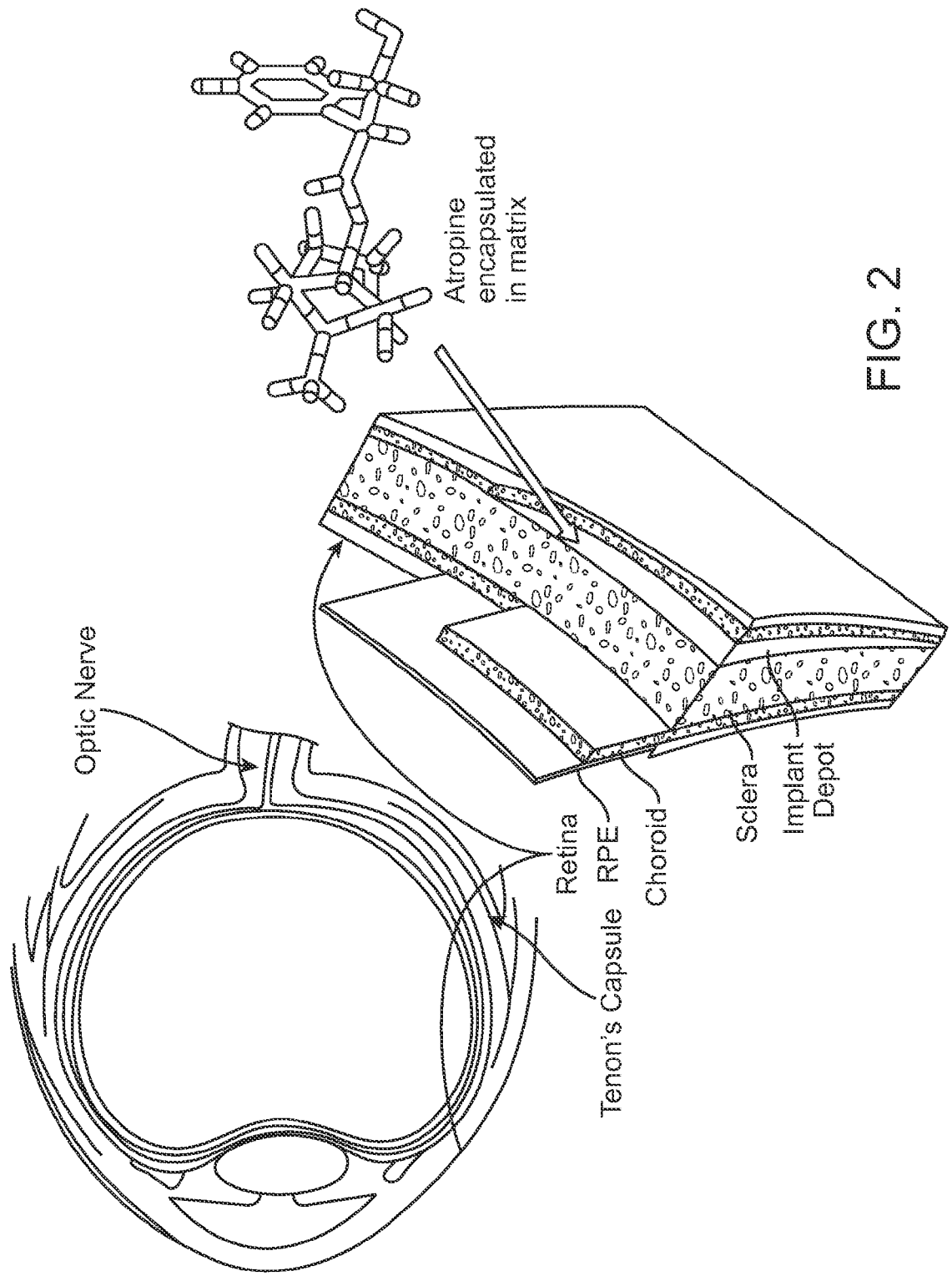
FIG. 2 depicts schematically the release of the muscarinic antagonist atropine at the sub-Tenon's capsule.

As used herein, the term "copolymer" describes a polymer which contains more than one type of subunit. The term encompasses polymer which include two, three, four, five, or six types of subunits.

The terms "subject," "individual," "host," and "patient" are used interchangeably herein to a member or members of any mammalian or non-mammalian species. Subjects and patients thus include, without limitation, humans, non-human primates, canines, felines, ungulates (e.g., equine, bovine, swine (e.g., pig)), avians, rodents (e.g., rats, mice), and other subjects. Non-human animal models, particularly mammals, e.g. a non-human primate, a murine (e.g., a mouse, a rat), lagomorpha, etc. may be used for experimental investigations.

"Treating" or "treatment" of a condition or disease includes: (1) preventing at least one symptom of the condition, i.e., causing a clinical symptom to not significantly develop in a mammal that may be exposed to or predisposed to the disease but does not yet experience or display symptoms of the disease, (2) inhibiting the disease, i.e., arresting or reducing the development of the disease or its symptoms, or (3) relieving the disease, i.e., causing regression of the disease or its clinical symptoms.

A "therapeutically effective amount" or "efficacious amount" means the amount of a compound that, when administered to a mammal or other subject for treating a disease, is sufficient, in combination with another agent, or alone in one or more doses, to effect such treatment for the disease. The "therapeutically effective amount" will vary depending on the compound, the disease and its severity and the age, weight, etc., of the subject to be treated.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the unit dosage forms depend on the particular compound employed and the effect to be achieved, and the pharmacodynamics associated with each compound in the host.

The term "physiological conditions" is meant to encompass those conditions compatible with living cells, e.g., predominantly aqueous conditions of a temperature, pH, salinity, etc. that are compatible with living cells.

A "pharmaceutically acceptable excipient," "pharmaceutically acceptable diluent," "pharmaceutically acceptable carrier," and "pharmaceutically acceptable adjuvant" means an excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. "A pharmaceutically acceptable excipient, diluent, carrier and adjuvant" as used in the specification and claims includes one and more than one such excipient, diluent, carrier, and adjuvant.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a hydrogel" includes a plurality of such hydrogels and reference to "the muscarinic antagonist" includes reference to one or more muscarinic antagonists and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides compositions and methods for treating ocular disorders such as myopia. The present disclosure provides a biodegradable hydrogel comprising a muscarinic antagonist. The present disclosure provides methods of treating ocular disorders such as myopia, the method generally involving implanting into an individual in need thereof an effective amount of a subject biodegradable hydrogel, where the biodegradable hydrogel is implanted into or around the eye.

Biodegradable Hydrogels

The present disclosure provides a biodegradable hydrogel comprising a muscarinic antagonist. A subject muscarinic antagonist-biodegradable hydrogel composition includes a muscarinic antagonist distributed within a biodegradable hydrogel. The muscarinic antagonist is in some embodiments not covalently linked to the hydrogel. In other embodiments, the muscarinic antagonist is covalently linked to a moiety within the hydrogel.

Muscarinic Antagonists

The present invention provides a biodegradable hydrogel comprising a muscarinic antagonist, and use of same for treating an ocular disorder. Muscarinic antagonists suitable for use in a subject composition and/or in a subject method include, but are not limited to, atropine; scopolamine; a muscarinic antagonist as disclosed in WO 97/16187; a 3-dihydro-1-{1-[piperidin-4-yl]piperidin-4-yl}-2H-benzimidazol-2-one as described in U.S. Pat. No. 5,691,323; a 1,3-dihydro-1-{4-amino-1-cyclohexyl}-2H-benzimidazol-2-one as described in U.S. Pat. No. 5,691,323; a 1-[cycloalkylpiperidin-4-yl]-2H benzimidazolone as described in U.S. Pat. No. 5,718,912; a tricyclic compound as described in U.S. Pat. No. 5,461,052; pirenzepine (5,11-Dihydro-11-[4-methyl-1-piperazinyl)acetyl]-6H-pyrido[2,3-b][1,4]benzo diazepin-6-one) or its dihydrochloride; telenzepine: 4,9-dihydro-3-methyl-4-[(4-methyl-(1)piperazine)acetyl]1OH-thieno-[3,4-b][1,5]-benzodiazepin-10-one, or its dihydrochloride; a 1,3-dihydro-1-[1-(1-heteroarylpiperidin-4-yl)piperidin-4-yl]-2H-benzimidazolone as described in U.S. Pat. No. 5,756,508; a benzimidazolidin-2-one derivatives 1-substituted with a 4-piperidinyl moiety which in turn is 1-substituted, as described in WO 96/13262; a muscarinic $M_2$ antagonist (e.g., imipramine, amitriptyline, nortriptyline, desipramine, 10-hydroxynortriptyline, and the like); himbacine ((3aR,4R,4aS,8aR,9aS)-4-{(E)-[(2R,6S)-1,6-dimethylpiperidin-2-yl]vinyl}-3-methyldecahydronaphtho[2,3-c]furan-1(3H)-one) and himbacine analogs (see, e.g., WO 2005/118576; and WO 2006/076564); homatropine ((N,N-dimethyl-8-azoniabicyclo[3.2.1]oct-3-yl)2-hydroxy-2-phenyl-acetate bromide); tropicamide (N-ethyl-3-hydroxy-2-phenyl-N-(pyridin-4-ylmethyl)propanamide); oxyphenonium (2-(2-Cyclohexyl-2-hydroxy-2-phenylacetoxy)-N,N-diethyl-N-methylethanaminium); oxyphenonium bromide; dexetimide(3-(1-benzyl-4-piperidyl)-3-phenyl-piperidine-2,6-dione); benztropine ((3-endo)-3-(diphenylmethoxy)-8-methyl-8-azabicyclo[3.2.1]octane); benztropine mesylate; 4-diphenylacetoxy-N-methyl-piperidine (4-DAMP); Hexahydro-siladifenidol (HHSiD); 2-Methylimidazol-1-yl-substituted analogs of HHSiD; p-fluoro-HHSiD; AF-DX 116 ([11-([2-[(diethylamino)methyl]-1-piperidinyl]acetyl)-5,11-dihydro-6H-pyrido[2,3-b][1,4]benzodiaze pine-6-one]); QNB (3-quinuclidinyl benzylate; 1-azabicyclo[2.2.2]oct-3-yl hydroxy (diphenyl)acetate); and the like.

Representative muscarinic antagonists include, but are not limited to, atropine, atropine sulfate, atropine oxide, methylatropine nitrate, homatropine hydrobromide, hyoscyamine (d, l) hydrobromide, scopolamine hydrobromide, ipratropium bromide, oxitropium bromide, tiotropium bromide, methantheline, propantheline bromide, anisotropine methyl bromide, clidinium bromide, copyrrolate (Robinul), isopropamide iodide, mepenzolate bromide, tridihexethyl chloride (Pathilone), hexocyclium methylsulfate, cyclopentolate hydrochloride, tropicamide, trihexyphenidyl hydrochloride, pirenzepine, telenzepine, AF-DX 116, and methoctramine.

Combinations of two or more of the aforementioned muscarinic antagonist can be included in a biodegradable hydrogel matrix. For example, in some embodiments, a subject biodegradable hydrogel matrix comprises both atropine and scopolamine. As another example, in some embodiments, a subject biodegradable hydrogel matrix comprises both atropine and tropicamide. As another example, in some embodiments, a subject biodegradable hydrogel matrix comprises both atropine and pirenzapine. As another example, in some embodiments, a subject biodegradable hydrogel matrix comprises both pirenzapine and tropicamide.

In some embodiments, a subject biodegradable hydrogel matrix comprises two muscarinic antagonists of different selectivities, e.g., two muscarinic antagonists selected from a nonselective muscarinic antagonist, an M1 muscarinic antagonist, an M2 muscarinic antagonist, an M3 muscarinic antagonist, an M4 muscarinic antagonist, and an M5 muscarinic antagonist. For example, in some embodiments, a subject biodegradable hydrogel matrix comprises both a nonselective muscarinic antagonist and an M1 muscarinic antagonist. For example, in some embodiments, a subject biodegradable hydrogel matrix comprises both an M1 and an M2 muscarinic antagonist. As another example, in some embodiments, a subject biodegradable hydrogel matrix comprises both pirenzipine (M1) and QNB (M2). As another example, in some embodiments, a subject biodegradable hydrogel matrix comprises both atropine (nonselective) and 4-DAMP (M3, M4, M5). As another example, in some embodiments, a subject biodegradable hydrogel matrix comprises both HHSid (M3) and AF-DX 116 (M2).

In some embodiments, a biodegradable hydrogel comprising a muscarinic antagonist ("a muscarinic antagonist-containing hydrogel") includes only one therapeutic agent, i.e., a single muscarinic antagonist. In other embodiments, a muscarinic antagonist-containing hydrogel comprises two or more different muscarinic antagonists. In other embodiments, a muscarinic antagonist-containing hydrogel comprises, in addition to a single muscarinic antagonist or two or more different muscarinic antagonists, one or more additional therapeutic agents ("active agents"). A non-limiting example of a suitable additional therapeutic agent is 7-methylxanthine. Further non-limiting examples of suitable additional therapeutic agents include retinoic acid analogs.

Biodegradable Hydrogels

The present disclosure provides a biodegradable hydrogel comprising a muscarinic antagonist. A suitable hydrogel is a polymer of two or more monomers, e.g., a homopolymer or a heteropolymer comprising multiple monomers. Suitable hydrogel monomers include the following: lactic acid, glycolic acid, acrylic acid, 1-hydroxyethyl methacrylate (HEMA), ethyl methacrylate (EMA), propylene glycol methacrylate (PEMA), acrylamide (AAM), N-vinylpyrrolidone, methyl methacrylate (MMA), glycidyl methacrylate (GDMA), glycol methacrylate (GMA), ethylene glycol, fumaric acid, and the like. Common cross linking agents include tetraethylene glycol dimethacrylate (TEGDMA) and N,N'-methylenebisacrylamide. The hydrogel can be homopolymeric, or can comprise co-polymers of two or more of the aforementioned polymers.

Exemplary hydrogels include, but are not limited to, a copolymer of poly(ethylene oxide) (PEO) and poly(propylene oxide) (PPO); Pluronic™ F-127 (a difunctional block copolymer of PEO and PPO of the nominal formula $EO_{100}$-$PO_{65}$-$EO_{100}$, where EO is ethylene oxide and PO is propylene oxide); poloxamer 407 (a tri-block copolymer consisting of a central block of poly(propylene glycol) flanked by two hydrophilic blocks of poly(ethylene glycol)); a poly(ethylene oxide)-poly(propylene oxide)-poly(ethylene oxide) co-polymer with a nominal molecular weight of 12,500 Daltons and a PEO:PPO ratio of 2:1); a poly(N-isopropylacrylamide)-base hydrogel (a PNIPAAm-based hydrogel); a PNIPAAm-acrylic acid co-polymer (PNIPAAm-co-AAc); poly(2-hydroxyethyl methacrylate); poly(vinyl pyrrolidone); and the like.

In some embodiments, the hydrogel is a temperature-sensitive hydrogel. In some embodiments, a temperature-sensitive hydrogel is a polyacrylic acid or derivative thereof, e.g., poly(N-isopropylacrylamide) gel, and the increase in temperature causes the hydrogel to contract, thereby forcing the active agent out of the hydrogel. Alternatively, the temperature-sensitive hydrogel is an interpenetrating hydrogel network of poly(acrylamide) and poly(acrylic acid), and the increase in temperature causes the hydrogel to swell, thereby allowing the active agent to diffuse out of the gel. The temperature required for triggering release of an active agent from the hydrogel is generally about normal body temperature, e.g., about 37° C.

As noted above, in some embodiments, the hydrogel comprises a muscarinic antagonist linked to one or more moieties in the hydrogel, or embedded in the hydrogel. In some embodiments, the muscarinic antagonist is a hydrophilic compound.

The hydrogel can be modified with one or more proteolytically cleavable crosslinks See, e.g., Kim and Healy (2003) Biomacromolecules 4:1214. One or more of the hydrogel polymers can be modified with a cell-binding moiety, e.g., a moiety that provides for binding to a cell-surface receptor. For example, a cell-binding moiety can include an Arg-Gly-Asp (RGD) peptide.

Nanoparticles or Microparticles Distributed within a Hydrogel

In some embodiments, a muscarinic antagonist is encapsulated within a nanoparticle or microparticle, and the muscarinic antagonist-containing nanoparticle or microparticle is distributed within a hydrogel. Thus, in some embodiments, a muscarinic antagonist is contained within a biodegradable microsphere, where a biodegradable microsphere comprises: a) a nanoparticle or a microparticle comprising one or more muscarinic antagonists; and b) a hydrogel matrix that forms an outer layer surrounding the nanoparticle or microparticle. The nanoparticle (or microparticle) can comprise an inner core comprising: i) a hydrophobic polymer; ii) a hydrophilic polymer linked to the hydrophobic polymer, where the hydrophobic polymer and the hydrophilic polymers together form a nanoparticle or microparticle, where the hydrophobic polymer forms an inner layer of the nanoparticle or microparticle, and the hydrophilic polymer forms an outer layer of the nanoparticle or microparticle. In some embodiments, the microsphere further comprises one or more additional therapeutic agents ("active agents").

A muscarinic antagonist can be present within the hydrophobic core of the nanoparticle or microparticle. In some embodiments, a muscarinic antagonist is present only within the hydrophobic core, e.g., within the space created by the hydrophobic polymer. In some embodiments, a muscarinic antagonist is present within the hydrophobic core, and the muscarinic antagonist not linked to any moiety of the nanoparticle or microparticle. In other embodiments, a muscarinic antagonist is present within the hydrophobic core, and the muscarinic antagonist is linked to one or more moieties present in the hydrophobic core, e.g., the muscarinic antagonist is linked to a poly-L-lactide polymer. In other embodiments, the muscarinic antagonist is linked to the hydrophilic polymer, e.g., in some embodiments, the muscarinic antagonist is linked to a poly(ethylene glycol) (PEG) (e.g., the muscarinic antagonist is linked to a reactive group present on derivatized PEG; e.g., the muscarinic antagonist is linked to an amine group present on derivatized PEG).

In some embodiments, a muscarinic antagonist is present within the hydrophobic core; and a second active agent is linked to the hydrophilic polymer. For example, where a muscarinic antagonist is present within the hydrophobic core, and a second active agent is linked to the hydrophilic polymer, the second active agent is hydrophilic. In other embodiments, a second active agent is present within the hydrophobic core; and a muscarinic antagonist is linked to the hydrophilic polymer. For example, where a second active agent is present within the hydrophobic core, and a muscarinic antagonist is linked to the hydrophilic polymer, the muscarinic antagonist is hydrophilic.

In some embodiments, a subject microsphere comprises a muscarinic antagonist and a second active agent, where the muscarinic antagonist is associated with or linked to the nanoparticle or microparticle (e.g., the muscarinic antagonist is present within the hydrophobic core, either free within the hydrophobic core, or linked to a hydrophobic polymer in the hydrophobic core, or is linked to a hydrophilic polymer in the nanoparticle or microparticle); and the second agent is linked to or associated with the hydrogel. In some of these embodiments, the muscarinic antagonist is hydrophobic and the second active agent is hydrophilic. Where a subject microsphere comprises a muscarinic antagonist and a second active agent, where the muscarinic antagonist is associated with or linked to the nanoparticle (or microparticle) and where the second active agent is associated with or linked to the hydrogel, a two-stage release profile is provided where the muscarinic antagonist is released from the hydrogel at a first rate and over a first time period, and the second active agent is released from the nanoparticle (or microparticle) at a second rate and over a second time period.

Nanoparticle and Microparticle Polymers

As noted above, in some embodiments, a subject biodegradable microsphere comprises: a) a nanoparticle or a microparticle comprising one or more muscarinic antagonists; and b) a hydrogel matrix that forms an outer layer surrounding the nanoparticle or microparticle. The nanoparticle or microparticle can have an average diameter of from about 1 nm to about 900 µm, e.g., the nanoparticle can have an average diameter of from about 1 nm to about 5 nm, from about 5 nm to about 25 nm, from about 25 nm to about 50 nm, from about 50 nm to about 75 nm, from about 75 nm to about 100 nm, from about 100 nm to about 200 nm, from about 200 nm to about 300 nm, from about 300 nm to about 400 nm, from about 400 nm to about 500 nm, from about 500 nm to about 600 nm, from about 600 nm to about 700 nm, from about 700 nm to about 800 nm, from about 800 nm to about 900 nm, from about 900 nm to about 1 µm, from about 1 µm to about 10 µm, from about 10 µm to about 25 µm, from about 25 µm to about 50 µm, from about 50 µm to about 75 µm, from about 75 µm to about 100 µm, from about 100 µm to about 200 µm, from about 200 µm to about 300 µm, from about 300 µm to about 400 µm, from about 400 µm to about 500 µm, from about 500 µm to about 600 µm, from about 600 µm to about 700 µm, from about 700 µm to about 800 µm, or from about 800 µm to about 900 µm.

The nanoparticle or microparticle comprises a hydrophobic polymer and a hydrophilic polymer. Suitable hydrophobic and hydrophilic polymers include biocompatible polymers comprising from about 50 to about 100,000 subunits, e.g., from about 50 subunits to about 100 subunits, from about 100 subunits to about 500 subunits, from about 500 subunits to about 1,000 subunits, from about 1,000 subunits to about 5,000 subunits, from about 5,000 subunits to about 10,000 subunits, from about 10,000 subunits to about 25,000 subunits, from about 25,000 subunits to about 50,000 subunits, or from about 50,000 subunits to about 100,000 subunits. In some embodiments, the linear polymer comprises more than 100,000 subunits.

The subunits can all be identical, e.g., the polymer is a homopolymer. In other embodiments, more than one species of subunit is present, e.g., the polymer is a heteropolymer or co-polymer. In some embodiments, the polymer is a linear polymer. In other embodiments, the polymer may include one or more branches.

Suitable polymers include natural polymers, semisynthetic polymers, and synthetic polymers. Suitable synthetic polymers include, but are not limited to, polymers or copolymers derived from polydioxane, polyphosphazene, polysulphone resins, poly(acrylic acid), poly(acrylic acid) butyl ester, poly(ethylene glycol), poly(propylene), polyurethane resins, poly(methacrylic acid), poly(methacrylic acid)-methyl ester, poly(methacrylic acid)-n butyl ester, poly(methacrylic acid)-t butyl ester, polytetrafluoroethylene, polyperfluoropropylene, poly N-vinyl carbazole, poly(methyl isopropenyl ketone), poly alphamethyl styrene, polyvinylacetate, poly(oxymethylene), poly(ethylene-co-vinyl acetate), a polyurethane, a poly(vinyl alcohol), and polyethylene terephthalate; ethylene vinyl alcohol copolymer (commonly known by the generic name EVOH or by the trade name EVAL); polybutylmethacrylate; poly(hydroxyvalerate); poly(L-lactic acid) or poly(L-lactide); poly(e-caprolactone); poly(lactide-co-glycolide); poly(hydroxybutyrate); poly(hydroxybutyrate-co-valerate); polydioxanone; polyorthoester; polyanhydride; poly(glycolic acid) (PGA); poly(D,L-lactide) (PDLL); poly(L-Lactide)(PLL); copolymers of PGA, PDLA, and/or PLA; poly(glycolic acid-co-trimethylene carbonate); polyphosphoester; polyphosphoester urethane; poly(amino acids); cyanoacrylates; poly(trimethylene carbonate); poly(iminocarbonate); copoly(ether-esters) (e.g., PEO/PLA); polyalkylene oxalates; polyphosphazenes; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; amorphous Teflon; and carboxymethyl cellulose.

Suitable hydrophobic polymers include poly(L-lactide), poly(glycolide), poly(e-caprolactone), copolymers of lactide and/or glycolide or/and poly(ε-caprolactone), hydrophobic peptides or a combination of hydrophobic peptides, polyurethanes. Any hydrophobic polymer that can form a micelle in water is suitable for use as a hydrophobic polymer. Suitable hydrophobic polymers include, e.g., poly(glycolide) or poly(glycolic acid); poly(ε-caprolactone); poly(D,L-lactide); poly(L-Lactide); copolymers of these and other polyesters; polyamides; polyanhydrides; polyurethanes; poly(ortho esters); poly(iminocarbonates). In some embodiments, the hydrophobic polymer of the nanoparticle (or microparticle) is poly-L-lactide.

Suitable hydrophilic polymers include, but are not limited to, poly(ethylene glycol); poly(vinyl alcohol); polyethers; poly(methacrylic acid); poly(acrylic acid); poly(HEMA); hyaluronic acid; and hyaluronate.

In some embodiments, the hydrophilic polymer of the nanoparticle or microparticle is a poly(ethylene glycol) polymer. Polyethylene glycol has the general formula R(O—CH$_2$—CH$_2$)$_n$O—R, where R is hydrogen or a protective group such as an alkyl or an alkanol group, and where n is an integer from 1 to 1000.

PEG having a molecular weight in a range of from about 2 kDa to about 100 kDa, can be used, where the term "about," in the context of PEG, indicates that in preparations of polyethylene glycol, some molecules will weigh more, some less, than the stated molecular weight. For example, PEG suitable for conjugation to IFN-α has a molecular weight of from about 2 kDa to about 5 kDa, from about 5 kDa to about 10 kDa, from about 10 kDa to about 15 kDa, from about 15 kDa to about 20 kDa, from about 20 kDa to about 25 kDa, from about 25 kDa to about 30 kDa, from about 30 kDa to about 40 kDa, from about 40 kDa to about 50 kDa, from about 50 kDa to about 60 kDa, from about 60 kDa to about 70 kDa, from about 70 kDa to about 80 kDa, from about 80 kDa to about 90 kDa, or from about 90 kDa to about 100 kDa.

In some embodiments, the PEG is linear. In other embodiments, the PEG is branched. Branched PEG derivatives such as those described in U.S. Pat. No. 5,643,575, "star-PEG's" and multi-armed PEG's such as those described in Shearwater Polymers, Inc. catalog "Polyethylene Glycol Derivatives 1997-1998." Star PEGs are described in the art including, e.g., in U.S. Pat. No. 6,046,305.

PEG has at least one hydroxyl group, e.g., a terminal hydroxyl group, which hydroxyl group can be modified to generate a functional group that is reactive with an amino group, e.g., an epsilon amino group of a lysine residue, a free amino group at the N-terminus of a polypeptide, or any other amino group such as an amino group of asparagine, glutamine, arginine, or histidine.

The PEG can be derivatized so that an active agent (e.g., a muscarinic antagonist) can be linked to the PEG polymer. Suitable derivatives of PEG that are reactive with the free carboxyl group at the carboxyl-terminus of a peptide include, but are not limited to PEG-amine, and hydrazine derivatives of PEG (e.g., PEG-NH—NH$_2$).

A PEG polymer can be derivatized such that it comprises a terminal thiocarboxylic acid group, —COSH, which selectively reacts with amino groups to generate amide derivatives. Because of the reactive nature of the thio acid, selectivity of certain amino groups over others is achieved. For example, —SH exhibits sufficient leaving group ability in reaction with N-terminal amino group at appropriate pH conditions such that the s-amino groups in lysine residues are protonated and remain non-nucleophilic. On the other hand, reactions under suitable pH conditions may make some of the accessible lysine residues to react with selectivity.

PEG can comprise a reactive ester such as an N-hydroxy succinimidate at the end of the PEG chain. Such an N-hydroxysuccinimidate-containing PEG molecule reacts with select amino groups at particular pH conditions such as neutral 6.5-7.5. For example, the N-terminal amino groups may be selectively modified under neutral pH conditions. However, if the reactivity of the reagent were extreme, accessible-NH$_2$ groups of lysine may also react.

An active agent (e.g., a muscarinic antagonist) can be coupled directly to PEG (i.e., without a linking group) through an amino group, a sulfhydryl group, a hydroxyl group, or a carboxyl group.

An active agent (e.g., a muscarinic antagonist) can be attached to the PEG via a linking group. The linking group is any biocompatible linking group, where "biocompatible" indicates that the compound or group is non-toxic and may be utilized in vitro or in vivo without causing injury, sickness, disease, or death. PEG can be bonded to the linking group, for example, via an ether bond, an ester bond, a thiol bond or an amide bond. Suitable biocompatible linking groups include, but are not limited to, an ester group, an amide group, an imide group, a carbamate group, a carboxyl group, a hydroxyl group, a carbohydrate, a succinimide group (including, for example, succinimidyl succinate (SS), succinimidyl propionate (SPA), succinimidyl butanoate (SBA), succinimidyl carboxymethylate (SCM), succinimidyl succinamide (SSA) or N-hydroxy succinimide (NHS)), an epoxide group, an oxycarbonylimidazole group (including, for example, carbonyldimidazole (CDI)), a nitro phenyl group (including, for example, nitrophenyl carbonate (NPC) or trichlorophenyl carbonate (TPC)), a trysylate group, an aldehyde group, an isocyanate group, a vinylsulfone group, a tyrosine group, a cysteine group, a histidine group or a primary amine.

A non-limiting example of a suitable co-polymer forming a nanoparticle or microparticle is a poly(lysine-g(lactide-b-ethylene glycol) terpolymer. Park and Healy (2003) *Bioconjugate Chem* 14: 31119. One or more of the hydrogel polymers can be modified with a cell-binding moiety, e.g., a moiety that provides for binding to a cell-surface receptor. For example, a cell-binding moiety can include an Arg-Gly-Asp (RGD) peptide.

Hydrogels

As noted above, in some embodiments, a subject biodegradable microsphere comprises: a) a nanoparticle or a microparticle comprising one or more muscarinic antagonists; and b) a hydrogel matrix that forms an outer layer surrounding the nanoparticle or microparticle. A hydrogel is a polymer comprising monomeric units. Suitable hydrogel monomers include the following: lactic acid, glycolic acid, acrylic acid, 1-hydroxyethyl methacrylate (HEMA), ethyl methacrylate (EMA), propylene glycol methacrylate (PEMA), acrylamide (AAM), N-vinylpyrrolidone, methyl methacrylate (MMA), glycidyl methacrylate (GDMA), glycol methacrylate (GMA), ethylene glycol, fumaric acid, and the like. Common cross linking agents include tetraethylene glycol dimethacrylate (TEGDMA) and N,N'-methylenebisacrylamide. The hydrogel can be homopolymeric, or can comprise co-polymers of two or more of the aforementioned polymers.

The hydrogel that surrounds the nanoparticle or microparticle is generally hydrophilic. Suitable polymers for inclusion in the hydrogel include, but are not limited to, poly(N-isopropylacrylamide); poly(N-isopropylacrylamide-co-acrylic acid); hyaluronic acid or hyaluronate; crosslinked hyaluronic acid or hyaluronate; PHEMA; or copolymers p(NIPAAm)-based sIPNs and other hydrogel sIPNs (semi-interpenetrating networks).

In some embodiments, the hydrogel is a temperature-sensitive hydrogel. In some embodiments, a temperature-sensitive hydrogel is a polyacrylic acid or derivative thereof, e.g., poly(N-isopropylacrylamide) gel, and the increase in temperature causes the hydrogel to contract, thereby forcing the active agent out of the hydrogel. Alternatively, the temperature-sensitive hydrogel is an interpenetrating hydrogel network of poly(acrylamide) and poly(acrylic acid), and the increase in temperature causes the hydrogel to swell, thereby allowing the active agent to diffuse out of the gel. The temperature required for triggering release of an active agent from the hydrogel is generally about normal body temperature, e.g., about 37° C.

As noted above, in some embodiments, the hydrogel comprises a muscarinic antagonist linked to one or more moieties in the hydrogel, or embedded in the hydrogel. In some embodiments, the muscarinic antagonist is a hydrophilic compound.

The hydrogel can be modified with one or more proteolytically cleavable crosslinks See, e.g., Kim and Healy (2003) Biomacromolecules 4:1214.

Treatment Methods

The present disclosure provides a method of treating an ocular disorder in an individual in need thereof, the method generally involving intraocular or peri-ocular implantation of an effective amount of a hydrogel comprising a muscarinic antagonist.

As a non-limiting example, muscarinic antagonist-containing hydrogel is injected, e.g., at the posterior pole of the eye. As a non-limiting example, a muscarinic antagonist-containing hydrogel is injected into the sub-Tenon's capsule. As a non-limiting example, a muscarinic antagonist-containing hydrogel is delivered via intra-orbital injection.

In some embodiments, an effective amount of a muscarinic antagonist-containing hydrogel is an amount that provides for at least a slowing of high myopia progression, e.g., such that the rate of progression is slowed by at least about 10%, at least about 15%, at least about 20%, at least about 25%, at least about 30%, at least about 40%, at least about 50%, or more than 50%.

In some embodiments, an effective amount of a muscarinic antagonist-containing hydrogel is an amount that is effective to improve corrected visual acuity by at least about 10%, at least about 15%, at least about 20%, at least about 25%, at least about 30%, at least about 40%, at least about 50%, or more than 50%.

In some embodiments, an effective amount of a muscarinic antagonist-containing hydrogel is an amount that is effective to improve low contrast visual acuity by at least about 10%, at least about 15%, at least about 20%, at least about 25%, at least about 30%, at least about 40%, at least about 50%, or more than 50%.

In some embodiments, an effective amount of a muscarinic antagonist-containing hydrogel is an amount that is effective to maintain or increase retinal thickness over time. Retinal thickness can be determined by, e.g., optical coherence tomography (OCT).

In some embodiments, an effective amount of a muscarinic antagonist-containing hydrogel is an amount that is effective to improve retinal function by at least about 10%, at least about 15%, at least about 20%, at least about 25%, at least about 30%, at least about 40%, at least about 50%, or more than 50%. Retinal function can be assessed by multifocal electroretinogram.

Whether a particular muscarinic antagonist, or an amount of a muscarinic antagonist, is effective to achieve a clinical benefit in treating myopia (e.g., high myopia), can be determined using an animal myopia model. For a chick model of myopia, see, e.g., Lawrence and Azar (2002)*Ophthalmol. Clin. North Am.* 14:127; and Schmid and Wildsoet (1997) *Ophthalmol. Physiol. Opt.* 17:61. For a guinea pig model of myopia, see, e.g., McFadden et al. (2004) *Vision Res.* 44:643.

Pharmaceutical Formulations

A muscarinic antagonist-containing hydrogel can be formulated with one or more pharmaceutically acceptable excipients. A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Unit dosage forms of a muscarinic antagonist-containing hydrogel for injection can comprise a hydrogel as described above, where the hydrogel comprises a muscarinic antagonist, a composition as a solution in sterile water, normal saline or another pharmaceutically acceptable carrier. A biocompatible hydrogel that comprises a muscarinic antagonist, as described above, is also referred to herein as "a muscarinic antagonist-containing hydrogel." A muscarinic antagonist-containing hydrogel will in some embodiments further comprise one or more additional therapeutic agents ("active agents").

The term "unit dosage form," as used herein, refers to physically discrete units suitable as unitary dosages for human and animal subjects, each unit containing a predetermined quantity of a subject microsphere comprising an active agent calculated in an amount sufficient to produce the desired effect in association with a pharmaceutically acceptable diluent, carrier or vehicle. The specifications for a subject microsphere depend on the particular active agent contained within the microsphere and the effect to be achieved, and the pharmacodynamics associated with each compound in the host.

The total volume of a muscarinic antagonist-containing hydrogel (e.g., a unit dosage form) that can be administered to the eye ranges from about 1 μl to about 1 ml, e.g., from about 1 μl to about 5 μl, from about 5 μl to about 10 μl, from about 10 μl to about 15 μl, from about 15 μl to about 25 μl, from about 25 μl to about 50 μl, from about 50 μl to about 75 μl, from about 75 μl to about 100 μl, from about 100 μl to about 200 μl, from about 200 μl to about 300 μl, from about 300 μl to about 500 μl, from about 500 μl to about 750 μl, or from about 750 μl to about 1 ml.

A unit dosage form of a muscarinic antagonist-containing hydrogel can include from about 1 ng to about 10 mg of an active agent, e.g., a muscarinic antagonist (and optionally one or more additional active agents).

Where a muscarinic antagonist-containing hydrogel comprises a microsphere (e.g., a nanoparticle or a microparticle contained within a hydrogel), a unit dosage form of a muscarinic antagonist-containing hydrogel can include from about $10^5$ to about $10^9$ microspheres, where a unit dosage form of a subject microsphere comprises from about 1 ng to about 10 mg of an active agent, e.g., a muscarinic antagonist (and optionally one or more additional active agents).

In some embodiments, multiple doses of a muscarinic antagonist-containing hydrogel are administered. The frequency of administration of a muscarinic antagonist-containing hydrogel can vary depending on any of a variety of factors, e.g., severity of the symptoms, etc. For example, in some embodiments, a muscarinic antagonist-containing hydrogel is administered once a year, once every six months, once every three months, once every two months, once per month, twice per month, three times per month, every other week (qow), once per week (qw), or twice per week (biw).

A muscarinic antagonist-containing hydrogel composition is administered to an individual typically using a localized route of administration (e.g., intra-ocular administration or peri-ocular administration, etc., via injection). Administration can be acute (e.g., of short duration, e.g., a single administration, administration for one day to one week), or chronic (e.g., of long duration, e.g., administration for longer than one week, e.g., administration over a period of time of from about 2 weeks to about one month, from about one month to about 3 months, from about 3 months to about 6 months, from about 6 months to about 1 year, or longer than one year).

Subjects Suitable for Treatment

Individuals in need of treatment with a subject method include individuals with myopia; individuals who have been treated for myopia; and individuals who have never been treated for myopia. "Myopia" includes simple myopia; degenerative myopia (e.g., malignant, pathological, or progressive myopia); and induced or acquired myopia. Myopia includes, low myopia (myopia of between zero and −3.00 diopters); medium myopia (myopia myopia of between −3.00 and −6.00 diopters); and high myopia (myopia of −6.00 diopters or less, e.g., ≤−6.00 diopters, e.g., from −6.00 diopters to −7.00 diopters, from −7.00 diopters to −8.00 diopters, from −8.00 diopters to −10.00 diopters, or less than −10.00 diopters). In some embodiments, the individual has degenerative myopia. In some embodiments, the individual has high myopia. In some embodiments, a subject method is suitable for treating high myopia progression. In some embodiments, the individual has, in addition to myopia, glaucoma. In some embodiments, the individual has, in addition to myopia, cataracts. In some embodiments, the individual has, in addition to myopia, retinal detachment. In some embodiments, the individual has, in addition to myopia, macular degeneration.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Implantation of a Biodegradable Hydrogel Matrix for Ocular Delivery of Atropine

Figure 3:
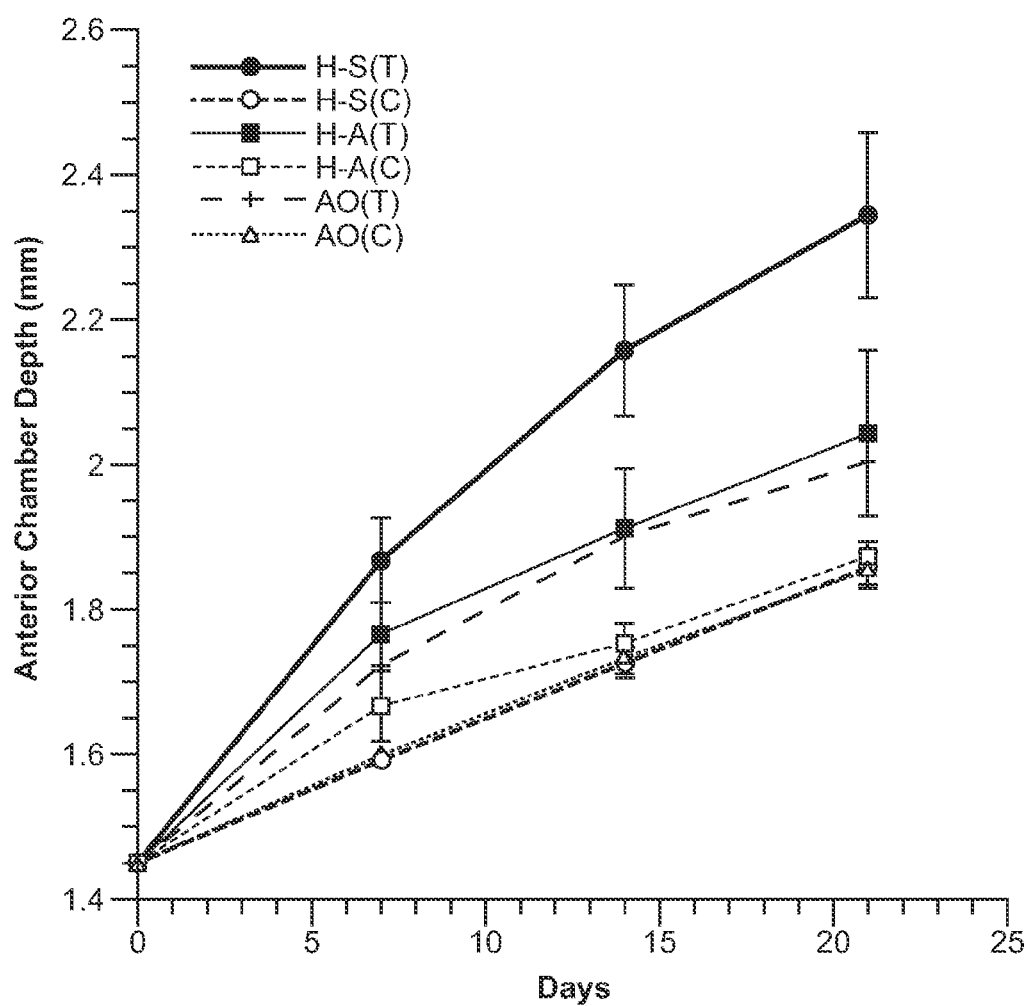
FIG. 3 depicts anterior chamber depth over 21 days following implantation into the posterior sclera of atropine in a biodegradable hydrogel matrix.
Figure 4:
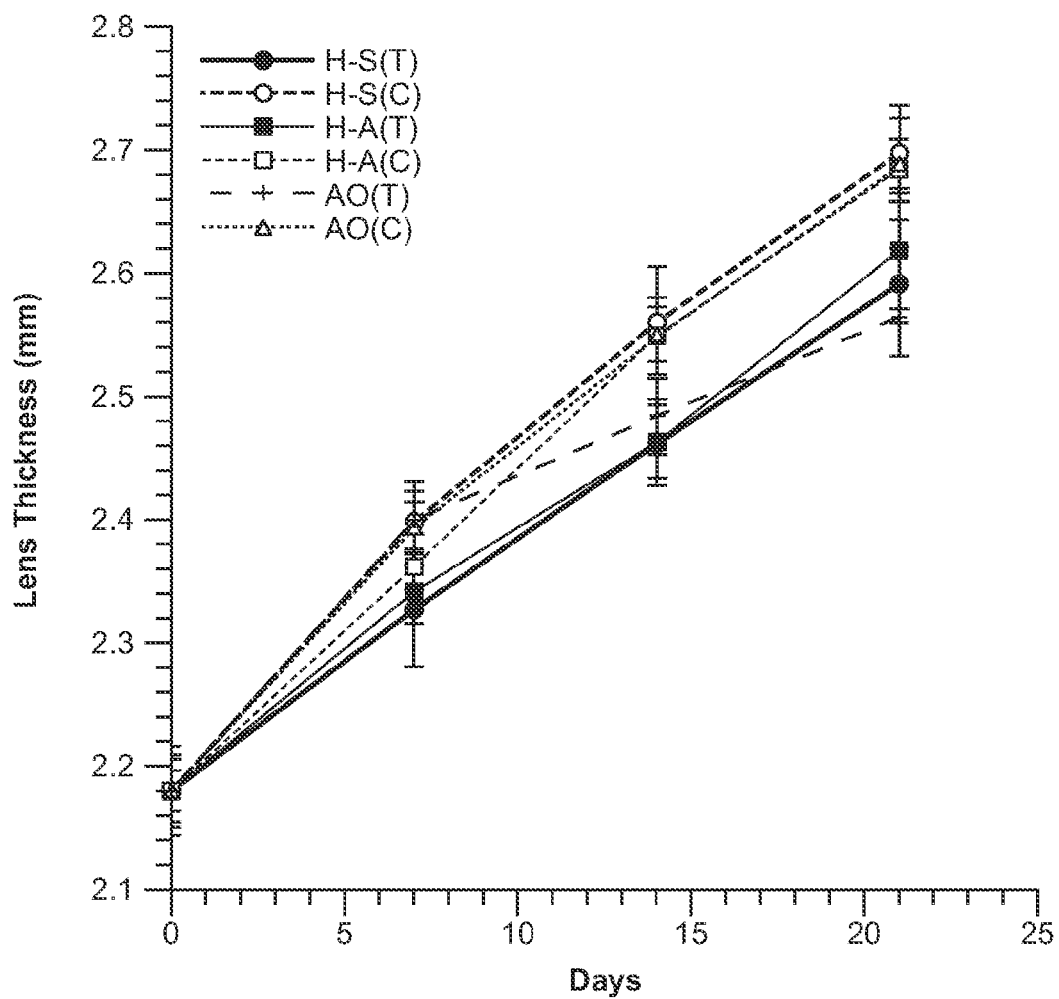
FIG. 4 depicts lens thickness over 21 days following implantation into the posterior sclera of atropine in a biodegradable hydrogel matrix.
Figure 5:
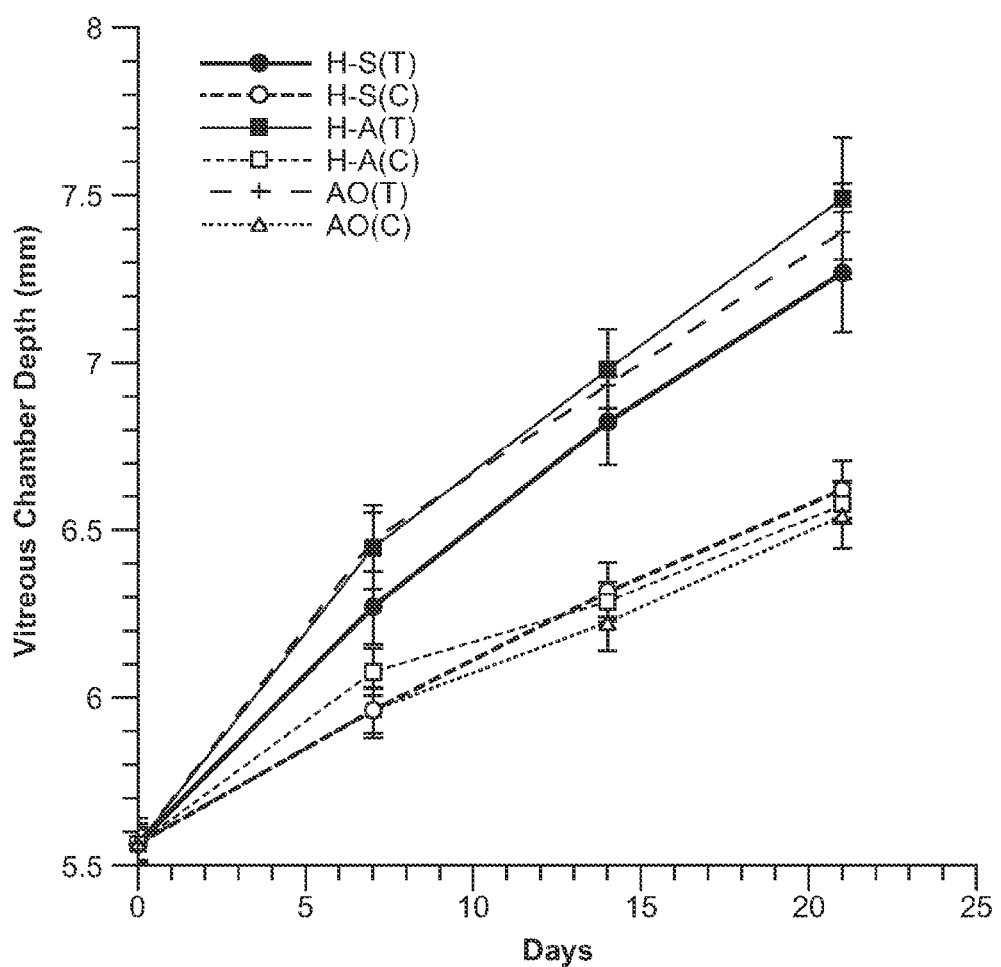
FIG. 5 depicts vitreous chamber depth over 21 days following implantation into the posterior sclera of atropine in a biodegradable hydrogel matrix.
Figure 6:
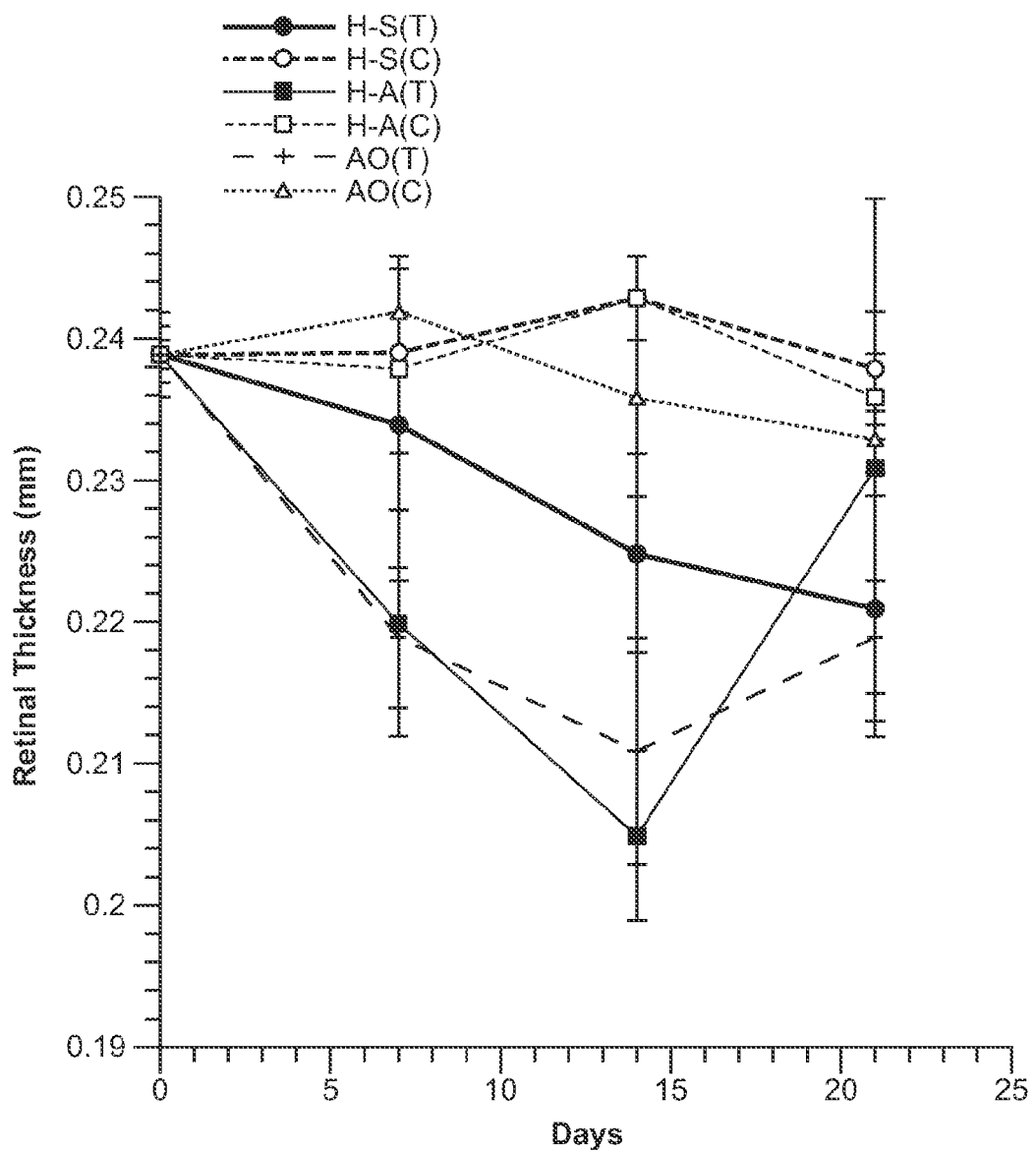
FIG. 6 depicts retinal thickness over 21 days following implantation into the posterior sclera of atropine in a biodegradable hydrogel matrix.
Figure 7:
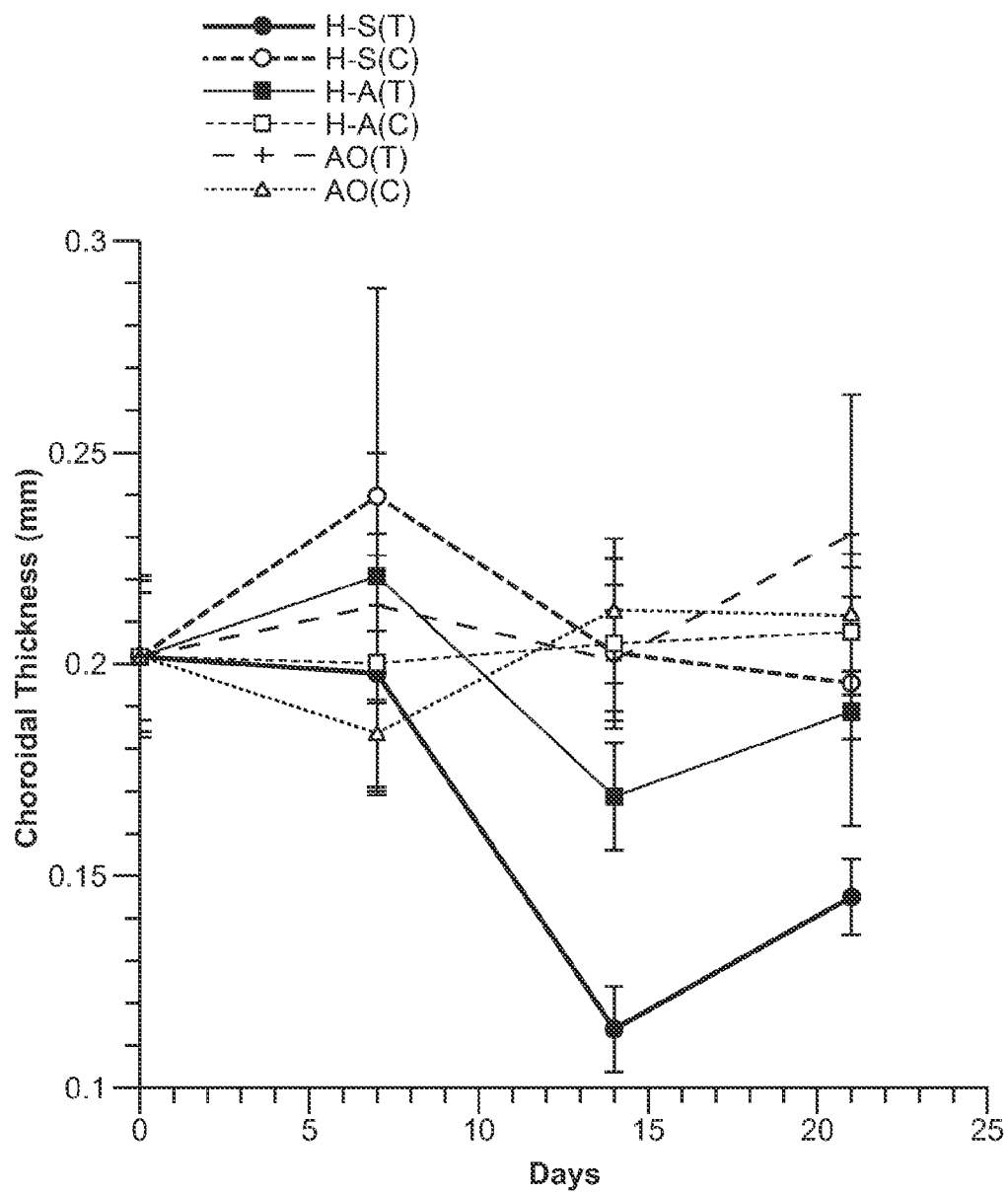
FIG. 7 depicts choroidal thickness over 21 days following implantation into the posterior sclera of atropine in a biodegradable hydrogel matrix.
Figure 8:
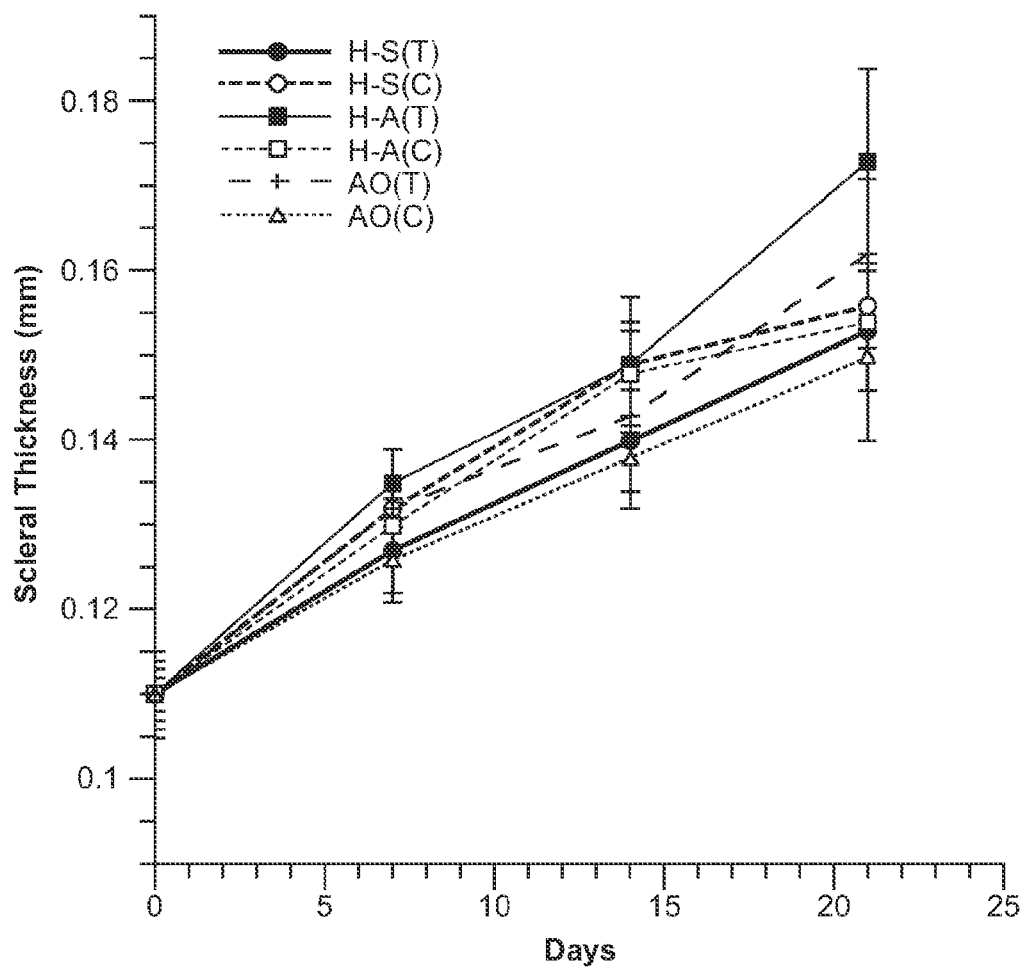
FIG. 8 depicts scleral thickness over 21 days following implantation into the posterior sclera of atropine in a biodegradable hydrogel matrix.
Figure 9:
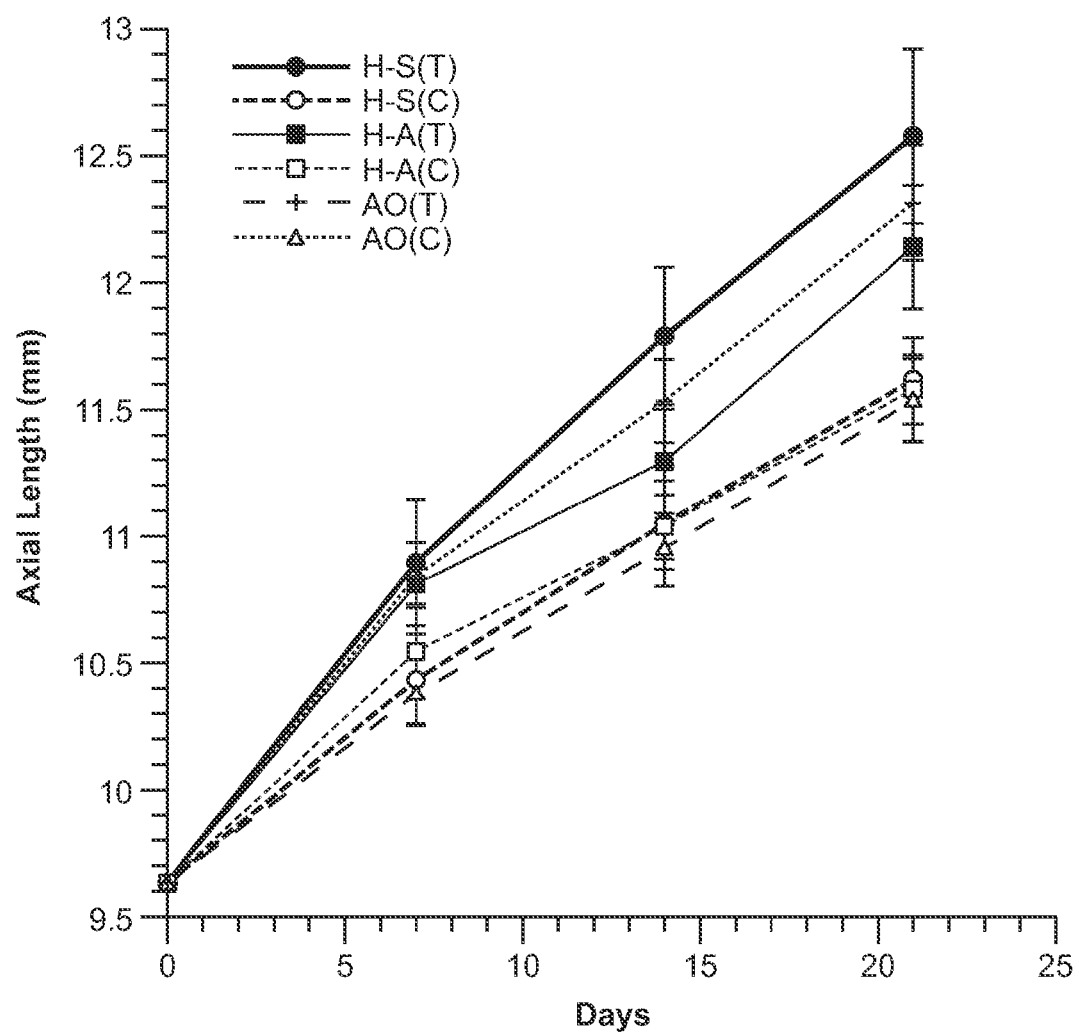
FIG. 9 depicts axial length over 21 days following implantation into the posterior sclera of atropine in a biodegradable hydrogel matrix.

Atropine was included in a poly(N-isopropylacrylamide)/acrylic acid co-polymer (PNIPAAm-co-AAC) hydrogel. A chick model was used to compare: Group 1) PNIPAAm-co-AAC hydrogel/atropine treatment by injection of the PNIPAAm-co-AAC hydrogel/atropine adjacent to the sclera at the posterior pole of the eye; Group 2) PNIPAAm-co-AAC hydrogel/saline (no atropine) treatment by injection of the PNIPAAm-co-AAC hydrogel/saline into the posterior pole of the eye; and Group 3) daily atropine eye drops (directly onto the lens). There were six animals in each group. As a control, the fellow eye of the treated was left untreated in each animal. Ocular dimensions data of treated and untreated (control) eyes were obtained over 21 days following treatment. The data are depicted in FIGS. 3-9.

H-S(T): hydrogel with saline (treated eye); H-S(C): untreated fellow eye;

H-A(T): hydrogel with atropine (treated eye); H-A(C): untreated fellow eye;

AO(T): atropine eye drop daily (treated eye); AO(C): untreated fellow eye.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of treating high myopia in an individual having high myopia, the method comprising administering to the individual an effective amount of a muscarinic antagonist-containing biodegradable hydrogel, wherein the hydrogel is selected from the groups consisting of a bifunctional block copolymer of poly(ethylene oxide) (PEO) and poly(propylene oxide) (PPO), a poly(N-isopropylacrylamide)-based hydrogel, or a poly(N-isopropylacrylamide)-acrylic acid copolymer, and poly(2-hydroxyethylene methacrylate), wherein the muscarinic antagonist-containing hydrogel is administered by intraorbital injection.

2. The method of claim 1, wherein the hydrogel is a bifunctional block copolymer of PEO and PPO.

3. The method of claim 1, wherein the hydrogel is a poly(N-isopropylacrylamide)-based hydrogel.

4. The method of claim 3, wherein the hydrogel is a poly(N-isopropylacrylamide)-acrylic acid copolymer.

5. The method of claim 1, wherein the hydrogel is comprises poly(2-hydroxyethylene methacrylate).

6. The method of claim 1, wherein the hydrogel comprises poly(vinyl pyrrolidone).

7. The method of claim 1, wherein the muscarinic antagonist is encapsulated in a nanoparticle or a microparticle.

8. The method of claim 7, wherein the nanoparticle comprises a hydrophobic polymer and a hydrophilic polymer, wherein the hydrophobic polymer forms a hydrophobic core.

9. The method of claim 8, wherein the hydrophilic polymer is a poly(ethylene glycol) polymer.

10. The method of claim 8, wherein the hydrophobic polymer is poly(L-lactide).

11. The method of claim 7, wherein the muscarinic antagonist is not linked to a nanoparticle polymer.

12. The method of claim 1, wherein the hydrogel comprises poly(N-isopropylacrylamide-co-acrylic acid).

13. The method of claim 1, wherein the muscarinic antagonist is atropine.

14. The method of claim 1, wherein the muscarinic antagonist is pirenzepine.

15. The method of claim 1, wherein the muscarinic antagonist is a combination of atropine and scopolamine.

16. The method of claim 1, wherein the muscarinic antagonist is a 1-[cycloalkylpiperidin-4-yl]-2H benzimidazolone.

17. The method of claim 1, wherein the muscarinic antagonist is telenzepine.

18. The method of claim 1, wherein the muscarinic antagonist-containing hydrogel is administered via intraorbital injection at the posterior pole.

19. The method of claim 1, wherein the muscarinic antagonist-containing hydrogel is administered via sub-Tenon's injection at the posterior pole.

20. The method of claim 1, wherein the individual is a human.

* * * * *